United States Patent [19]
Boell et al.

[11] 4,144,239
[45] Mar. 13, 1979

[54] MANUFACTURE OF PYRIDOXIN

[75] Inventors: Walter Boell, Dannstadt-Schauernheim; Horst Koenig, Ludwigshafen, both of Fed. Rep. of Germany

[73] Assignee: BASF Aktiengesellschaft, Ludwigshafen, Fed. Rep. of Germany

[21] Appl. No.: 896,165

[22] Filed: Apr. 14, 1978

[30] Foreign Application Priority Data

Apr. 20, 1977 [DE] Fed. Rep. of Germany ....... 2717478

[51] Int. Cl.$^2$ ............................................ C07D 213/67
[52] U.S. Cl. ..................... 546/301; 546/302; 546/303
[58] Field of Search ...................... 260/297.5, 295.5 R

[56] References Cited

U.S. PATENT DOCUMENTS 2,680,743   6/1954   Stevens ............................ 260/297.5

FOREIGN PATENT DOCUMENTS 72-34713   1/1972   Japan ..................................... 260/297.5

OTHER PUBLICATIONS

McCasland et al, Journal Org. Chem., vol. 26, pp. 3541–3543, (1961).
Stanton et al., Journal Am. Chem. Soc., vol. 61, pp. 3307–3310, (1939).

*Primary Examiner*—Alan L. Rotman
*Attorney, Agent, or Firm*—Keil & Witherspoon

[57] ABSTRACT

An industrially advantageous process for the manufacture of vitamin B6 (pyridoxin) from 2-methyl-3-hydroxy-4,5-bis-(halomethyl)-pyridine, wherein the starting compound is first converted in the conventional manner to the corresponding pure acetoxy compound which is reacted with an alkali metal acetate, alkaline earth metal acetate or tertiary ammonium acetate to give pyridoxin triacetate, from which pyridoxin can be liberated by hydrolysis or trans-esterification.

5 Claims, No Drawings

MANUFACTURE OF PYRIDOXIN

The present invention relates to a process for the manufacture of vitamin B6 (pyridoxin) from 2-methyl-3-hydroxy-4,5-bis-(halomethyl)-pyridine, in which the starting compound is first converted to the corresponding acetoxy compound and then to pyridoxin triacetate, from which pyridoxin is finally obtained by hydrolysis or trans-esterification.

In some of the possible methods of synthesizing vitamin B6 disclosed in the literature, important intermediates obtained are 2-methyl-3-hydroxy-4,5-bis-chloromethyl-pyridine (pyridoxin 4,5-dichloride; Ia) and 2-methyl-3-hydroxy-4,5-bis-bromomethylpyridine (pyridoxin 4,5-dibromide: Ib) (cf., for example, J. Am. Chem. Soc. 61 (1939) 3307, J. Org. Chem. 26 (1961) 3541 and U.S. Pat. No. 2,680,743 (1954)), from which pyridoxin can, in theory, be obtained by direct hydrolysis. In practice, however, this hydrolysis presents considerable problems. For example, direct hydrolysis of Ia or Ib in boiling water always gives a mixture of pyridoxin and the inner pyridoxin ether of the formula IV

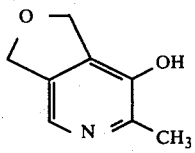

(IV)

(cf. J. Amer. Chem. Soc. 61 (1939) 3309). The proportion of the pyridoxin ether can be more than 50%. When an attempt is made to hydrolyze Ia with alkali, solutions of a very dark color are always obtained, from which it is only possible to isolate heavily contaminated pyridoxin in poor yield (cf. J. Org. Chem. 26 (1961) 3542); in some cases, a high-melting precipitate, presumed to be of polymeric nature, separates out (cf. J. Org. Chem. 26 (1961), 3541). It is true that pyridoxin can be obtained by reaction with sodium acetate in glacial acetic acid, followed by hydrolysis of the pyridoxin 4,5-diacetate (cf. Japanese Pat. No. 7,234,713), but the product obtained is so heavily contaminated by pyridoxin derivatives of unknown structure, presumably again of a polymeric nature, that repeated recrystallization is necessary to give pure pyridoxin.

It is object of the present invention to provide a process by means of which pyridoxin can be obtained in a very pure form, and in high yields, from Ia or Ib.

We have found, surprisingly, that this object is achieved and that pyridoxin is obtained in a very pure form and in good yields from Ia or Ib by first converting the pyridoxin 4,5-dihalide to the 3-acetoxy compound, reacting the latter with an alkali metal acetate, alkaline earth metal acetate or tertiary ammonium acetate to give pyridoxin triacetate and only then isolating pyridoxin from the latter by hydrolysis or trans-esterification.

Accordingly, the present invention relates to a process for the manufacture of pyridoxin from 2-methyl-3-hydroxy-4,5-bis-(halomethyl)-pyridine, wherein A. the starting compound of the general formula I

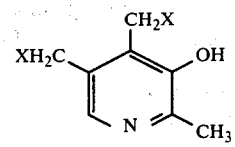

(I)

where X is Cl or Br, is first converted in the conventional manner (acetylated) to the novel 2-methyl-3-acetoxy-4,5-bis-(halomethyl)-pyridine of the formula II

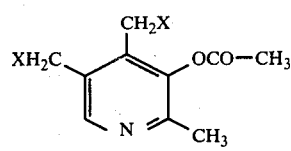

(II)

B. this compound is converted, by reaction with an alkali metal acetate, alkaline earth metal acetate or tertiary ammonium acetate, into the pyridoxin triacetate, and C. the latter, following optional purification by distillation under reduced pressure, is hydrolyzed or trans-esterified to liberate pyridoxin.

The starting compounds Ia and Ib are intermediates obtained in various conventional synthesis of vitamin B6. For example, they are obtained by reaction of HCl or HBr with pyridoxin ethers, for example with pyridoxin 4,5-dimethyl ether or with the inner ether of pyridoxin IV (cf. J. Am. Chem. Soc. 61 (1939) 3307; J. Org. Chem. 26 (1961) 3541; and U.S. Pat. No. 2,680,743 (1954)).

In the case of the inner pyridoxin ether IV, in particular, only the reaction with hydrogen halides, for example treatment with boiling hydrobromic acid or with hydrochloric acid at about 130° C. under pressure, has proved a practicable method of ether cleavage. The hydrochloric acid can also be replaced by anhydrous solvents, eg. glacial acetic acid, in which case hydrogen chloride gas is forced in under similar conditions to those described above. The yield in all cases mentioned is about 90% of theory. The pyridoxin 4,5-dihalide formed precipitates as the hydrohalide from the reaction solution and can be filtered off. It does not require purification before being reacted further.

Re (A)

Suitable acetylating agents for converting Ia or Ib to the corresponding 3-acetoxy compound are acetic anhydride, acetyl chloride and ketene, the first-mentioned being preferred. Suitable solvents for this stage of the process include glacial acetic acid and those aprotic solvents which dissolve an appreciable amount of Ia or Ib under the reaction conditions. Examples are dimethylformamide, dimethylsulfoxide, acetic anhydride, ethylglycol acetate (1-ethoxy-2-acetoxy-ethane), ethyl acetate and butyl acetate. The reaction temperature is in general from 30° to 140° C., preferably from 50° to 100° C. Below 30° C., the reaction becomes uneconomically slow, whilst above 140° C. decomposition can occur. The reaction time is generally from about 10 minutes to 5 hours, depending on the reaction temperature. The progress of the reaction can be followed by NMR spectroscopy or IR spectroscopy or by thin layer chromatography. The yield is virtually quantitative.

Re (B)

Suitable alkali metal acetates are, in general, Li-ac, Na-ac and K-ac, whilst suitable alkaline earth metal acetates are Mg-ac$_2$, Ca-ac$_2$, Sr-ac$_2$ and Ba-ac$_2$. Examples of tertiary ammonium acetates are triethylammonium, tri-n-propyl-ammonium, tri-iso-propyl-ammonium, tri-n-butyl-ammonium, tri-iso-butylammonium, tri-2-ethyl-hexyl-ammonium, N,N-dimethylisobutylammonium, N,N-dimethyl-2-ethylhexylammonium, N,N-dimethylcyclohexyl-ammonium, N,N-dimethyl-benzyl-ammonium and N,N-dimethyl-2-dimethylaminoethyl-ammonium acetate. Na-ac, K-ac, triethylammonium acetate and tripropylammonium acetate are preferred. Suitable solvents include, in addition to those mentioned for stage A, the tertiary amines on which the tertiary ammonium salts are based, eg. triethylamine, tri-n-propylamine, tri-iso-propylamine, tri-n-butylamine, tri-iso-butylamine, tri-2-ethylhexylamine, N,N-dimethylisobutylamine, N,N-dimethyl-2-ethylhexylamine, N,N-dimethyl-cyclohexylamine, N,N-dimethylbenzylamine and N,N,N',N'-tetramethylethylenediamine.

The reaction temperature is in general from 40° to 140° C., preferably from 70° to 110° C., and the reaction time is generally from about 0.5 to 5 hours, depending on the reaction temperature. The yield of pyridoxin 3,4,5-triacetate is in general about 90% of theory.

In a preferred embodiment, the two process stages are combined, so that the same solvent is used and the intermediate II is not isolated before it is reacted further. If acetic acid is used as the solvent, the salt of acetic acid required for the preparation of the pyridoxin triacetate can be produced by simply adding a tertiary amine to the reaction mixture (see Example 2).

An additional advantage of the process of the invention is that it is possible to purify the resulting pyridoxin 3,4,5-triacetate by distillation under reduced pressure and hence to remove impurities originating from the intermediates. This advantageous means of purification is particularly important since products which are used for pharmacological purposes have to conform to very high purity standards.

Re (C)

The pyridoxin 3,4,5-triacetate can be converted to pyridoxin by acid or alkaline hydrolysis. Since essentially only pyridoxin hydrochloride is marketed, hydrolysis in dilute hydrochloric acid or trans-esterification with an alcohol after passing hydrogen chloride gas into the mixture are of particular importance. In the former case, a solution of pyridoxin 3,4,5-triacetate in dilute hydrochloric acid, containing at least the equivalent amount of acid, is heated. In the latter case, pyridoxin 3,4,5-triacetate is dissolved in an alcohol, eg. methanol, ethanol, isobutanol or 2-methoxyethanol, at least the equivalent amount of HCl gas is passed in and the mixture is heated, whereupon pyridoxin hydrochloride precipitates as crystals. Instead of using pure alcohol, the acetate of the alcohol, containing at least a stochiometric amount of the free alcohol, may also be used as the solvent. The reaction temperature is in general from 40° to 120° C. and the reaction time is from 30 minutes to 4 hours, depending on the temperature. The yield is virtually quantitative in every case.

In a particular embodiment of the process described, the ether cleavage of the inner pyridoxin ether IV is combined with the reaction stages according to the invention. For this purpose, the pyridoxin ether is converted to the corresponding soluble pyridoxin ether 3-acetate by means of an acylating agent, eg. acetic anhydride, acetyl chloride or ketene, in acetic acid solution, and the pyridoxin ether 3-acetate is converted, in the same reaction medium, to Ia by means of hydrogen chloride gas at about 130° C. and under pressure, the water of reaction liberated during the ether cleavage being bonded by hydrolysis of the acetate group, so that the reaction medium remains anhydrous. An acylating agent is then added to the reaction mixture which contains Ia, and the mixture is heated; after adding a tertiary amine, the mixture is again heated, whereupon pyridoxin 3,4,5-triacetate is formed. After isolation, this compound is distilled and hydrolyzed or transesterified, to form pyridoxin hydrochloride. Accordingly, conversion of the pyridoxin ether to pyridoxin 3,4,5-triacetate takes place, to all intents and purposes, in an easily performed one-vessel reaction.

The compounds 2-methyl-3-acetoxy-4,5-bis-(chloromethyl)-pyridine and 2-methyl-3-acetoxy-4,5-bis-(bromomethyl)-pyridine which are formed as intermediates in the process of the invention, and their hydrochlorides and hydrobromides, are novel compounds. Pyridoxin ether acetate has also not been described previously. On the other hand, pyridoxin triacetate has been known for a long time (see U.S. Pat. No. 2,349,267). However, it has hitherto been prepared by acetylating pyridoxin.

With the process of the invention, the 2-methyl-3-hydroxy-4,5-bis-(halomethyl)-pyridines are converted into a purer pyridoxin in a very simple manner and with very good yields, as compared with the conventional methods.

EXAMPLE 1

A. Preparation of 2-methyl-3-hydroxy-4,5-bis-(chloromethyl)-pyridine hydrochloride (pyridoxin dichloride hydrochloride; Ia)

(a) In hydrochloric acid 151 g (1 mole) of the inner pyridoxin ether IV and 300 ml of concentrated hydrochloric acid were heated for 6 hours at 130° C. in a 1 liter tantalum autoclave. The pressure was brought to a constant value of 10 atmospheres gauge by introducing hydrogen chloride gas (90 g of HCl were taken up). After cooling, and releasing the pressure, the crystals were filtered off, washed with 50 ml of concentrated hydrochloric acid and dried for 1 hour at 70° C./20 mm Hg. 209 g (0.86 mole) of pyridoxin dichloride hydrochloride of metlting point 201°–203° C. were obtained.

After concentrating the mother liquor to about ⅓ of its volume, a further 7.5 g (30 millimoles) of dichloride crystallized out; melting point 179°–184° C.

(b) In glacial acetic acid 302 g (2 moles) of the inner pyridoxin ether IV were heated with 1 liter of glacial acetic acid at 130° C. in a tantalum autoclave. After forcing in 365 g (10 moles) of hydrogen chloride, the mixture was kept for 6 hours at the same temperature (maximum pressure 20 atmospheres gauge), and was then allowed to cool, and let down. Pyridoxin dichloride hydrochloride which crystallized out was filtered off, washed with 0.25 liter of glacial acetic acid and dried for 1 hour at 70° C./20 mm Hg. 442 g of pyridoxin dichloride hydrochloride of melting point 202°–203° C. were obtained. Yield of 91%.

B. 2-Methyl-3-acetoxy-4,5-bis-(chloromethyl)-pyridine hydrochloride 126 g (1.2 moles) of 97% pure acetic anhydride were added to 243 g (1 mole) of the pyridoxin dichloride hydrochloride obtained above, in 1 liter of dry dimethylformamide, and the mixture was heated for 1 hour at 60°–65° C. After about 7 minutes, solution occurred and after 15 minutes a thick suspension of the product precipitated.

A sample was filtered off; melting point 173°–175° C.

NMR spectra δ-values in D-dimethylsulfoxide: 2.45 ($CH_3$); 4.82, 5.0 (—$CH_2$—); 8.65 (—H); 2.45 ($CH_3$—$CO_2$—).

Elementary analysis:
Calculated: C = 42.2; H = 4.2; Cl = 37.4; N = 4.9.
Found: C = 42.0; H = 4.2; Cl = 37.6; N = 5.0.

C. Pyridoxin triacetate (III)

328 g (4 moles) of anhydrous sodium acetate were added, whilst stirring, to the above suspension and the mixture was heated for 2.5 hours at 80°–85° C. When it had cooled to about 5°–10° C., the sodium chloride which had precipitated, and the excess sodium acetate, were filtered off and washed with a little DMF. The DMF solution was substantially concentrated on a rotary evaporator under reduced pressure. 328 g of oily pyridoxin triacetate were obtained.

After distillation under greatly reduced pressure, through an air-cooled descending condenser, 263 g of colorless pyridoxin triacetate which solidified on triturating and which was pure according to NMR spectroscopy, were obtained. Yield 89%. Boiling point 140°–145° C./$10^{-2}$ mm Hg; melting point 45° C.

D. Pyridoxin hydrochloride (a) 28 g of hydrogen chloride were passed, in the course of 15 minutes, into a solution of 147.5 g (0.5 mole) of distilled pyridoxin triacetate in 250 ml of methanol, during which time the temperature rose to 50°–60° C. The reaction mixture was then refluxed for 1.5 hours. The resulting suspension was cooled to about 10° C. and the precipitate thereby formed was filtered off, washed with 40 ml of cold methanol and dried for 1 hour at 70° C./20 mm Hg. 101.5 g of pure pyridoxin hydrochloride of melting point 207°–209° C. were obtained; yield 99%.

(b) In a different embodiment, the methanol solvent was replaced by a mixture of 200 ml of methyl acetate and 80 ml (2 moles) of ethanol. The other conditions, and the result, remained the same.

EXAMPLE 2

Pyridoxin triacetate

A mixture of 121.5 g (0.5 mole) of pyridoxin dichloride hydrochloride, 100 g (1.67 moles) of glacial acetic acid and 79 g (0.75 mole) of 97% pure acetic anhydride was heated for 2 hours at 95° C., during which time the conversion to 2-methyl-3-acetoxy-4,5-bis-(chloromethyl)-pyridine hydrochloride took place completely and the product crystallized out. Whilst cooling this mixture to about 80° C., 230 g (1.6 moles) of tri-n-propylamine were added as rapidly as possible (in the course of 4–6 minutes) and the reaction mixture was then heated for 2.5 hours at 90°–95° C. After it had cooled, the mixture was taken up in 400 ml of toluene and 540 g of 20% strength sodium hydroxide solution (2.7 moles) were added at a temperature not exceeding 20° C. The organic phase was separated off and the aqueous phase was again extracted with 100 ml of toluene. After stripping off the toluene and tri-n-propylamine (boiling point 60° C./20 mm Hg), crude pyridoxin triacetate remained. Its distillation through an air-cooled descending condenser gave 131 g of pure colorless pyridoxin triacetate of boiling point 140°–145° C./$10^{-2}$ mm Hg; yield 89%.

The pyridoxin triacetate obtained was converted to pyridoxin hydrochloride by the method described in Example 1 D.

EXAMPLE 3

A. 2-Methyl-3-hydroxy-4,5-bis-(bromomethyl)-pyridine hydrobromide (pyridoxin dibromide hydrobromide; Ib)

151 g (1 mole) of the inner pyridoxin ether IV and 1.5 liters of 48% strength hydrobromic acid were boiled for 2.5 hours. At the same time the water of reaction was removed through a 20 cm high column filled with glass rings; the boiling point was 104° C. initially and 124° C. finally. 323 ml of distillate (21% strength hydrobromic acid) were obtained.

After the reaction mixture had cooled to 10° C., the precipitate formed was filtered off, washed with 150 ml of hydrobromic acid and dried for 1 hour at 70° C./20 mm Hg. 338 g of pyridoxin dibromide hydrobromide were obtained as colorless crystals of melting point 226°–227° C.; yield 90%.

The mother liquor was concentrated to about 300 ml, refluxed for 45 minutes and cooled, and the precipitate formed was filtered off. A further 27 g of pyridoxin dibromide hydrobromide were obtained as light brown crystals of melting point 226°–227° C. Yield 7%.

B + C. Pyridoxin triacetate (III)

47.0 g (125 millimoles) of pyridoxin dibromide hydrobromide were dissolved in 125 ml of anhydrous DMF and after adding 16 g (150 millimoles) of 97% pure acetic anhydride the mixture was heated for 1.25 hours at 60°–65° C., whereupon the 2-methyl-3-acetoxy-4,5-bis-(bromomethyl)-pyridine hydrobromide II which had formed crystallized out partially. 49 g (0.5 mole) of anhydrous potassium acetate were added to the suspension whilst cooling it slightly, to 50°–60° C. When the exothermic reaction had subsided, the reaction mixture was heated for 1.5 hours at 80° C. and then cooled to 5°–10° C.; the potassium bromide which had precipitated, and the excess potassium acetate, were filtered off and the filter cake was washed twice, each time with 30 ml of DMF. The DMF solution was substantially concentrated on a rotary evaporator under reduced pressure. The residue was suspended in 200 ml of toluene; 5.0 g of salt remained undissolved. The toluene solution was concentrated and the residue was distilled through an air-cooled descending condenser. Yield: 33.6 g (91%) of colorless pyridoxin triacetate which is pure according to NMR spectroscopy. Boiling point 140°–145°/$10^{-2}$ mm Hg.

D. Pyridoxin hydrochloride

A solution of 29.5 g (0.1 mole) of distilled pyridoxin triacetate in 55 ml of 2N hydrochloric acid was boiled for 2 hours. After stripping off the solvent and drying the residue for 1 hour at 70° C./1 mm Hg, 20.0 g of pyridoxin hydrochloride of melting point 205°–207° C. remained. Yield 97.5%.

EXAMPLE 4

A. Pyridoxin dichloride hydrochloride via pyridoxin ether 3-acetate 22.7 g (150 millimoles) of the inner pyridoxin ether IV, 60 ml of glacial acetic acid and 17.3 g of 97% pure acetic anhydride were heated for 1.5 hours at 105°–110° C. The solution was concentrated under reduced pressure. Distillation of the residue through an air-cooled descending condenser gave 28.5 g of the novel pyridoxin ether 3-acetate V of boiling point 112°–115° C./0.2 mm Hg; melting point 71° C.; yield 98%.

NMR spectra: δ-values in CDCl$_3$: 2.4 (CH$_3$—); 4.9 and 5.7 (—CH$_2$—); 8.18 (H—) and 2.3 (CH$_3$—CO$_2$—).

Elementary analysis:
Calculated: C = 62.2; H = 5.7; N = 7.2.
Found: C = 62.0; H = 5.7; N = 7.3.

A solution of pyridoxin ether 3-acetate in glacial acetic acid, as obtained by heating a mixture of 150 millimoles of the pyridoxin ether IV, 60 ml of glacial acetic acid and 17.3 g of 97% pure acetic anhydride (total volume 90 ml), was heated at 130° C. in a 250 ml tantalum autoclave. Hydrogen chloride was forced in repeatedly to bring the pressure to 20 atmospheres gauge. After 28 g of HCl had been absorbed in the course of 4 hours, no further HCl was taken up. After a total of 6 hours at 130° C., the reaction mixture was cooled and let down.

B + C. Pyridoxin triacetate III

The slurry of pyridoxin dichloride hydrochloride obtained as described in Example 4A was concentrated by distilling off 75 ml of acetic acid. After adding 24 g (225 millimoles) of 97% pure acetic anhydride, the reaction mixture was heated for 2 hours at 95° C., 69 g (0.48 mole) of tri-n-propylamine were then added in the course of 4–6 minutes at 80° C., and the batch was heated for 2.5 hours at 90°–95° C.

When it had cooled, the mixture was taken up in 120 ml of ethylene chloride and 162 g of 20% strength sodium hydroxide solution (0.81 mole) were added at a temperature of not more than 20° C. The organic phase was separated off and the aqueous phase was extracted with a further 30 ml of ethylene chloride. After stripping off the ethylene chloride and tri-n-propylamine, 42 g of crude pyridoxin triacetate remained. Distillation through an air-cooled descending condenser gave 35.5 g of pure pyridoxin triacetate having a boiling point of about 150° C./0.1 mm Hg. Yield: 80%.

The pyridoxin triacetate obtained was converted to pyridoxin hydrochloride by the method described in Example 1 D.

We claim:
1. A process for the manufacture of pyridoxin from a 2-methyl-3-hydroxy-4,5-bis-(halomethyl)-pyridine of the general formula I

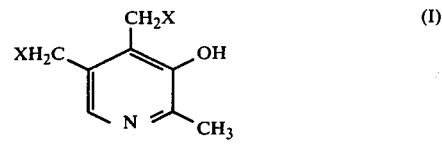

where X is Cl or Br, wherein
A. the compound of the general formula I is acetylated to form a 2-methyl-3-acetoxy-4,5-bis-(halomethyl)-pyridine of the general formula II

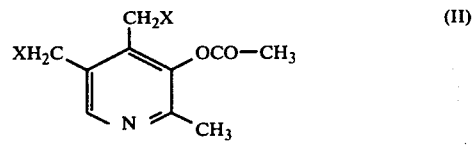

B. this compound is converted by reaction with an alkali metal acetate, alkaline earth metal acetate or tertiary ammonium acetate into pyridoxin triacetate, and
C. the latter compound is hydrolyzed or trans-esterified to liberate pyridoxin.

2. A process as claimed in claim 1, wherein the compound of formula I is acetylated by reaction with acetic anhydride.

3. A process as claimed in claim 1, wherein the acetylation is carried out in glacial acetic acid or an aprotic solvent for the compound of formula I under the reaction conditions and the conversion of the compound of formula II is carried out in such a solvent or in a tertiary amine.

4. A process as claimed in claim 3, wherein the compound of formula II is not isolated but is reacted with the acetate salt in the same solvent as has been used for the acetylation.

5. A process as claimed in claim 1, wherein the pyridoxin triacetate is purified by distillation under reduced pressure prior to hydrolysis or trans-esterification.

* * * * *